US009662006B2

(12) United States Patent
Dai et al.

(10) Patent No.: US 9,662,006 B2
(45) Date of Patent: *May 30, 2017

(54) ACCOMMODATION COMPENSATION SYSTEMS AND METHODS

(71) Applicant: AMO Development, LLC, Santa Ana, CA (US)

(72) Inventors: Guang-ming Dai, Fremont, CA (US); Leander Zickler, Menlo Park, CA (US)

(73) Assignee: AMO Development, LLC, Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/175,179

(22) Filed: Jun. 7, 2016

(65) Prior Publication Data

US 2016/0287066 A1    Oct. 6, 2016

Related U.S. Application Data

(60) Division of application No. 14/956,104, filed on Dec. 1, 2015, now Pat. No. 9,439,561, which is a
(Continued)

(51) Int. Cl.
  *A61B 3/10*    (2006.01)
  *A61B 3/00*    (2006.01)
(Continued)

(52) U.S. Cl.
  CPC .......... *A61B 3/0025* (2013.01); *A61B 3/107* (2013.01); *A61B 3/1015* (2013.01); *A61B 3/112* (2013.01);
(Continued)

(58) Field of Classification Search
  CPC ........... A61B 3/103; A61B 3/14; A61B 3/107; A61B 3/125; A61B 3/1015; G02C 13/005
(Continued)

(56) References Cited

U.S. PATENT DOCUMENTS 4,665,913 A   5/1987   L'Esperance, Jr.
4,669,466 A   6/1987   L'Esperance
(Continued)

FOREIGN PATENT DOCUMENTS

AU   2008256709 B2   9/2012
EP      2146621 A1   1/2010
WO   2008148038 A1  12/2008

OTHER PUBLICATIONS

Castellucci et al., One aberration leads to another in the optical components of the eye, Retreived from the internet: , 1 page.
(Continued)

*Primary Examiner* — Dawayne A Pinkney
(74) *Attorney, Agent, or Firm* — Abbott Medical Optics Inc.

(57) ABSTRACT

Methods and systems for obtaining an ocular aberration measurement of an eye of a patient are provided. Exemplary techniques involve obtaining a first induced metric for the eye that corresponds to a first accommodation state of the eye, obtaining a second induced metric for the eye that corresponds to a second accommodation state of the eye, and determining a natural metric of the eye based on the first and second induced metrics. An induced metric may include a pupil size or a spherical aberration. Techniques can also include determining a target metric for the eye base on the natural metric, determining whether an actual metric of the eye meets the target metric, obtaining an ocular aberration measurement of the eye if the actual metric meets the target metric, and determining a treatment for the eye based on the ocular aberration measurement.

20 Claims, 11 Drawing Sheets

Related U.S. Application Data continuation of application No. 14/466,701, filed on Aug. 22, 2014, now Pat. No. 9,198,572, which is a continuation of application No. 14/013,311, filed on Aug. 29, 2013, now Pat. No. 8,851,670, which is a continuation of application No. 13/541,217, filed on Jul. 3, 2012, now Pat. No. 8,545,016, which is a continuation of application No. 13/276,704, filed on Oct. 19, 2011, now Pat. No. 8,251,509, which is a continuation of application No. 13/012,298, filed on Jan. 24, 2011, now Pat. No. 8,057,038, which is a continuation of application No. 12/126,185, filed on May 23, 2008, now Pat. No. 7,901,077.

(60) Provisional application No. 60/940,014, filed on May 24, 2007.

(51) Int. Cl.
   *A61B 3/11* (2006.01)
   *A61B 3/107* (2006.01)
   *A61F 9/008* (2006.01)
   *G02C 7/04* (2006.01)
   *A61B 3/14* (2006.01)

(52) U.S. Cl.
   CPC ............ *A61B 3/14* (2013.01); *A61F 9/008* (2013.01); *A61F 9/00804* (2013.01); *G02C 7/041* (2013.01); *A61F 2009/0087* (2013.01); *A61F 2009/0088* (2013.01); *A61F 2009/00872* (2013.01); *A61F 2009/00895* (2013.01); *A61F 2009/00897* (2013.01)

(58) Field of Classification Search
   USPC ........ 351/204–206, 200, 211–212, 246–247, 351/219
   See application file for complete search history.

(56) References Cited

U.S. PATENT DOCUMENTS

| | | | |
|---|---|---|---|
| 4,732,148 A | 3/1988 | L'Esperance, Jr. | |
| 4,770,172 A | 9/1988 | L'Esperance, Jr. | |
| 4,773,414 A | 9/1988 | L'Esperance, Jr. | |
| 5,108,388 A | 4/1992 | Trokel | |
| 5,163,934 A | 11/1992 | Munnerlyn | |
| 5,207,668 A | 5/1993 | L'Esperance, Jr. | |
| 5,219,343 A | 6/1993 | L'Esperance, Jr. | |
| 5,646,791 A | 7/1997 | Glockler | |
| 5,683,379 A | 11/1997 | Hohla | |
| 5,713,892 A | 2/1998 | Shimmick | |
| 5,807,379 A | 9/1998 | L'Esperance, Jr. | |
| 6,004,313 A | 12/1999 | Shimmick et al. | |
| 6,095,651 A | 8/2000 | Williams et al. | |
| 6,203,539 B1 | 3/2001 | Shimmick et al. | |
| 6,271,915 B1 | 8/2001 | Frey et al. | |
| 6,315,413 B1 | 11/2001 | Shimmick et al. | |
| 6,331,177 B1 | 12/2001 | Munnerlyn et al. | |
| 7,387,387 B2 | 6/2008 | Dai | |
| 7,434,936 B2 | 10/2008 | Dai et al. | |
| 7,513,620 B2 | 4/2009 | Dai et al. | |
| 7,547,102 B2 | 6/2009 | Dai | |
| 7,901,077 B2 | 3/2011 | Dai et al. | |
| 7,922,328 B2 | 4/2011 | Dai et al. | |
| 8,057,038 B2 | 11/2011 | Dai et al. | |
| 8,251,509 B2 | 8/2012 | Dai et al. | |
| 8,545,016 B2 | 10/2013 | Dai et al. | |
| 8,851,670 B2 | 10/2014 | Dai et al. | |
| 9,198,572 B2 | 12/2015 | Dai et al. | |
| 2003/0007124 A1 | 1/2003 | Levine | |
| 2003/0071967 A1 | 4/2003 | Campin et al. | |
| 2004/0169820 A1 | 9/2004 | Dai et al. | |
| 2005/0057723 A1 | 3/2005 | Wakil et al. | |
| 2005/0122474 A1 | 6/2005 | Koretz | |
| 2005/0280777 A1 | 12/2005 | Dai | |
| 2006/0023162 A1 | 2/2006 | Azar et al. | |
| 2008/0143963 A1* | 6/2008 | Lindacher | G02C 7/028 351/246 |
| 2009/0066915 A1 | 3/2009 | Lai | |
| 2011/0013140 A1 | 1/2011 | Lai | |

OTHER PUBLICATIONS

Cheng H., et al., "A population study on changes in wave aberrations with accommodation," Journal of Vision, 2004, vol. 4(4), pp. 272-280.

Fernandez E.J., et al., "Study on the Effects of Monochromatic Aberrations in the Accommodation Response by Using Adaptive Optics," Journal of the Optical Society of America A, 2005, vol. 22 (9), pp. 1732-1738.

He J.C., et al., "Monochromatic Aberrations in the Accommodated Human Eye," Vision Research, 2000, vol. 40 (1), 41-48.

International Search Report and Written Opinion for Application No. PCT/US2008/064758, mailed on Sep. 5, 2008, 17 pages.

Nguyen-Khoa et al., "Changes in aberrations with accommodation as a function of age," retrieved from http://www.imagine-eyes.com, pp. 1.

Palikaris et al., "Objective measurement of wavefront aberrations with and without accommodation," Journal of Refractive Surgery, pp. S602-S605, 2007, vol. 17(5), Thorofare, NJ, USA.

* cited by examiner

ACCOMMODATION COMPENSATION SYSTEMS AND METHODS

CROSS-REFERENCES TO RELATED APPLICATIONS

This application is a divisional of U.S. patent application Ser. No. 14/956,104, filed Dec. 1, 2015, which is a continuation of U.S. patent application Ser. No. 14/466,701, filed Aug. 22, 2014, (now U.S. Pat. No. 9,198,572 issued Dec. 1, 2015), which is a continuation of U.S. patent application Ser. No. 14/013,311 filed Aug. 29, 2013 (now U.S. Pat. No. 8,851,670 issued Oct. 7, 2014), which is a continuation of U.S. patent application Ser. No. 13/541,217 filed Jul. 3, 2012, (now U.S. Pat. No. 8,545,016 issued Oct. 1, 2013), which is a continuation of U.S. patent application Ser. No. 13/276,704 filed Oct. 19, 2011, (now U.S. Pat. No. 8,251,509 issued Aug. 28, 2012), which is a continuation of U.S. patent application Ser. No. 13/012,298 filed Jan. 24, 2011, (now U.S. Pat. No. 8,057,038 issued Nov. 15, 2011), which is a continuation of U.S. patent application Ser. No. 12/126,185 filed May 23, 2008, (now U.S. Pat. No. 7,901,077 issued Mar. 8, 2011), which claims the benefit of U.S. Provisional Patent Application No. 60/940,014 filed May 24, 2007. This application is also related to U.S. patent application Ser. Nos. 10/872,331 and 11/156,257, filed Jun. 17, 2004 Jun. 17, 2005 respectively. The entire disclosure of each of these filings is incorporated herein by reference for all purposes.

BACKGROUND OF THE INVENTION

Embodiments of the present invention relate to systems, devices, and methods for compensating voluntary and other accommodation of patients during ocular diagnostic and treatment procedures. In particular, embodiments provide techniques for improving the accuracy of ocular aberration measurements and the development of vision correction treatments by evaluating accommodation in a patient.

An ocular wavefront measurement can change dramatically as the eye accommodates and the lens shape changes. This measurement change can be manifested in a Hartmann-Shack spot pattern as a pincushion effect. Current wavefront-based refractometers often derive a patient's total refraction, or total ocular aberration, from a single measurement under the assumption that accommodation has been effectively suppressed. Yet patients can experience some degree of instrument myopia when such measurements are taken, as the eye tends to accommodate inappropriately when viewing though an optical instrument. For example, when a patient looks through an optical instrument such as a refractometer or an aberrometer, the eye often responds by accommodating more than would be necessary for natural viewing. In some cases this excess accommodation, or instrument myopia, can be on the order of several diopters. As a result, the effect of instrument myopia can lead to an inaccurate measurement of refraction.

A variety of approaches have been proposed to eliminate instrument myopia. In some cases, a doctor may try to simulate the object being viewed, for example a viewing target, as far away from the patient as possible such that the target is closer to optical infinity. When an eye is gazing at a far distance the eye lens is thin and relaxed, and accommodation is reduced. Another technique that attempts to cause eye to relax the accommodation mechanism involves fogging. Fogging can involve adding a small amount of plus sphere power with a convex spherical lens, to provide a slight overcorrection. When the eye is optically fogged, vision becomes blurrier as the eye accommodates, and thus accommodation is discouraged. Additional techniques involve asking the patient to relax their vision. However many patients do not respond as desired to such approaches. Even when these accommodation-elimination techniques are implemented some instrument myopia may persist. What is more, it is often difficult to determine whether the eye is accommodated or not, particularly when a doctor or other instrument operator making such a determination is inexperienced.

What is needed are systems and methods for reducing the amount of instrument myopia present in the eye during an optical measurement. Moreover, improved techniques are desired for determining residual accommodation of the eye. Relatedly, there is a need for systems and methods that can accurately determine whether a patient's eye is accommodated, or the degree to which the patient's eye is accommodated. Embodiments of the present invention provide solutions to at least some of these problems.

BRIEF SUMMARY OF THE INVENTION

Systems, methods, and software are provided for compensating voluntary accommodation in a patient eye during a wavefront measurement. These approaches can be used to improve the accuracy of the ocular aberration measurement, and to improve the treatment of patients using laser vision correction of wavefront-driven procedures. Moreover, these approaches can be used to measure the residual accommodation of presbyopic patients to customize or optimize a presbyopic treatment. Embodiments of the present invention provide improved techniques for evaluating the accommodation state of a patient's eye, as well as for eliminating, reducing, or compensating for unwanted accommodation. For example, embodiments may encompass method and techniques for determining the amount of accommodation in an eye, determining the degree to which an eye is accommodated, the accommodation status of an eye, and the like. Similarly, embodiments encompass methods of designing optical treatment shapes for vision correction, such as presbyopia refraction shapes, based on the accommodation characteristics of the patient eye. These shapes are well suited for implementation in any of a variety of vision correction modalities, including accommodating IOLs, custom IOLs, contact lenses, laser vision correction, and the like.

In a first aspect, embodiments of the present invention provide methods of obtaining an ocular aberration measurement of an eye of a patient. Methods can include obtaining a first induced metric for the eye that corresponds to a first accommodation state of the eye, obtaining a second induced metric for the eye that corresponds to a second accommodation state of the eye, and determining a natural metric of the eye based on the first and second induced metrics. In some cases, the first induced metric can include a first induced pupil size or a first induced spherical aberration, the second induced metric can include a second induced pupil size or a second induced spherical aberration, and the natural metric can include a natural pupil size or a natural spherical aberration. Methods can also include determining a target metric for the eye base on the natural metric. A target metric can include a target pupil size or a target spherical aberration. In some cases, methods include determining whether an actual metric of the eye meets the target metric. Methods can also include alerting an operator if the actual metric does not meet the target metric. In some cases, an actual metric includes an actual pupil size or an actual spherical aberration. Methods can also include obtaining an ocular aberration measurement of the eye if the actual metric meets the target metric. An ocular aberration measurement can include a wavescan aberrometer examination, a contact lens aberrometer examination, an IOL aberrometer examination, or the like. In some cases, methods include determining a treatment for the eye based on the ocular aberration measurement. Methods can also include administering the treatment to the eye.

In another aspect, embodiments of the present invention encompass methods of obtaining an ocular aberration measurement of an eye of a patient, which can involve obtaining a first induced metric for the eye that corresponds to a first viewing condition, obtaining a second induced metric for the eye that corresponds to a second viewing condition, determining a difference between the first induced metric and the second induced metric, and determining an accommodation characteristic of the eye if the difference between the first induced metric and the second induced metric does not exceed a threshold. In some cases, methods can include determining a target metric based on the accommodation characteristic, determining whether an actual metric of the eye meets the target metric, and obtaining an ocular aberration measurement of the eye if the actual metric meets the target metric. In some cases, a first induced metric includes a first induced pupil size, a second induced metric includes a second induced pupil size, and an accommodation characteristic includes a minimally accommodated pupil size. A target metric can include a target pupil size, and an actual metric can include an actual pupil size. A first induced metric can include a first induced spherical aberration, a second induced metric can include a second induced spherical aberration, and an accommodation characteristic can include an minimally accommodated spherical aberration. In some cases, a target metric includes a target spherical aberration, and an actual metric includes an actual spherical aberration. An ocular aberration measurement can include, for example, a wavescan aberrometer examination, a contact lens aberrometer examination, an IOL aberrometer examination, or the like. In some cases, methods include alerting an operator if the actual metric does not meet the target metric. Methods can also include determining a treatment for the eye based on an ocular aberration measurement. Similarly, methods can include administering the treatment to the eye.

In some aspects, embodiments of the present invention encompass methods of determining a presbyopia treatment for an eye of a patient. Methods can include, for example, obtaining a first induced metric for the eye that corresponds to a first viewing condition, obtaining a second induced metric for the eye that corresponds to a second viewing condition, determining a difference between the first induced metric and the second induced metric, determining an accommodation characteristic of the eye if the difference between the first induced metric and the second induced metric does not exceed a threshold, determining a residual accommodation of the eye based on the accommodation characteristic, obtaining an ocular aberration measurement of the eye, and determining a presbyopia treatment for the eye based on the residual accommodation and the ocular aberration measurement. In some cases, a first induced metric includes a first induced pupil size, a second induced metric includes a second induced pupil size, an accommodation characteristic includes a maximally accommodated pupil size, a target metric includes a target pupil size, and an actual metric includes an actual pupil size. A first induced metric can include a first induced spherical aberration, a second induced metric can include a second induced spherical aberration, an accommodation characteristic can include an maximally accommodated spherical aberration, a target metric can include a target spherical aberration, and an actual metric can include an actual spherical aberration. An ocular aberration measurement can include a wavescan aberrometer examination, a contact lens aberrometer examination, an IOL aberrometer examination, or the like. In some cases, methods include administering the presbyopia treatment to the eye.

In another aspect, embodiments of the present invention include systems for obtaining an ocular aberration measurement of an eye of a patient. A system may include, for example, a first input configured to receive a first induced metric for the eye that corresponds to a first accommodation state of the eye, a second input configured to receive a second induced metric for the eye that corresponds to a second accommodation state of the eye, and a module configured to determine a natural metric of the eye based on the first and second induced metrics. A first induced metric can include a first induced pupil size or a first induced spherical aberration, a second induced metric can include a second induced pupil size or a second induced spherical aberration, and a natural metric can include a natural pupil size or a natural spherical aberration.

In a further aspect, embodiments of the present invention include systems for obtaining an ocular aberration measurement of an eye of a patient, which can include a first input configured to receive a first induced metric for the eye that corresponds to a first viewing condition, a second input configured to receive a second induced metric for the eye that corresponds to a second viewing condition, a first module configured to determine a difference between the first induced metric and the second induced metric, and a second module configured to determine an accommodation characteristic of the eye if the difference between the first induced metric and the second induced metric does not exceed a threshold. In some cases, systems can include a module configured to determine a target metric based on the accommodation characteristic, a module configured to determine whether an actual metric of the eye meets the target metric, and a module configured to receive an ocular aberration measurement of the eye if the actual metric meets the target metric.

In some aspects, embodiments of the present invention encompass systems for determining a presbyopia treatment for an eye of a patient. Systems can include, for example, an input configured to receive a first induced metric for the eye that corresponds to a first viewing condition, an input configured to receive a second induced metric for the eye that corresponds to a second viewing condition, a module configured to determine a difference between the first induced metric and the second induced metric, a module configured to determine an accommodation characteristic of the eye if the difference between the first induced metric and the second induced metric does not exceed a threshold, a module configured to determine a residual accommodation of the eye based on the accommodation characteristic, a module configured to receive an ocular aberration measurement of the eye, and a module configured to determine a presbyopia treatment for the eye based on the residual accommodation and the ocular aberration measurement.

In some aspect, embodiments of the present invention provide a method of obtaining a residual accommodation measurement of an eye of a patient. The method may include, for example, obtaining a first induced metric for the eye that corresponds to a first viewing condition, obtaining a second induced metric for the eye that corresponds to a second viewing condition, determining if a difference between the first induced metric and the second induced metric exceeds a threshold, determining an accommodation characteristic of the eye if the difference between the first induced metric and the second induced metric does not exceed the threshold, and determining the residual accommodation measurement of the eye based on the accommodation characteristic. In some cases, the first induced metric comprises a first induced pupil size, the second induced metric comprises a second induced pupil size, and the accommodation characteristic comprises a maximally accommodated pupil size. In some cases, the first induced metric comprises a first induced spherical aberration, the second induced metric comprises a second induced spherical aberration, and the accommodation characteristic comprises a maximally accommodated spherical aberration.

In some aspects, embodiments of the present invention provide a method of determining a natural metric of an unaccommodated eye. The method may include, for example, inputting a first induced metric for the eye that corresponds to a first accommodation state of the eye, inputting a second induced metric for the eye that corresponds to a second accommodation state of the eye, and determining the natural metric of the unaccommodated or minimally accommodated eye based on the first and second induced metrics and the first and second accommodation states of the eye. For example, the first and second induced metrics can be input into an input module, and the natural metric can be determined by a determination module. The natural metric can be an aberration metric or a pupil size metric. Optionally, the method may include inputting three or more induced metrics corresponding to respective accommodation states of the eye, and determining the natural metric of the unaccommodated or minimally accommodated eye based on a combination of two or more of the induced metrics. The aberration metric can be a spherical aberration metric, a sphere metric, or a coma metric. The method may also include determining a target metric for the unaccommodated or minimally accommodated eye based on the natural metric. Further, the method may include determining an actual metric of the eye. In some cases, the method may include determining whether the actual metric meets the target metric. The method may also include obtaining an ocular aberration measurement of the eye if the natural metric meets a target metric. The ocular aberration measurement can include, for example, a wavescan measurement. In some cases, the unaccommodated or minimally accommodated eye has a power of zero diopters.

In some aspects, embodiments encompass a method of determining a natural pupil size metric of an unaccommodated or minimally accommodated eye. The method can include inputting a first induced pupil size metric for the eye that corresponds to a first accommodation state of the eye, inputting a second induced pupil size metric for the eye that corresponds to a second accommodation state of the eye, and determining the natural pupil size metric of the unaccommodated or minimally accommodated eye based on the first and second induced pupil size metrics and the first and second accommodation states of the eye.

For a fuller understanding of the nature and advantages of the present invention, reference should be had to the ensuing detailed description taken in conjunction with the accompanying drawings.

DETAILED DESCRIPTION OF THE INVENTION

The present invention can be readily adapted for use with existing laser systems, wavefront measurement systems, and other optical measurement devices. Although the systems, software, and methods of the present invention are described primarily in the context of a laser eye surgery system, it should be understood the present invention may be adapted for use in alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom intraocular lenses, custom contact lenses, custom corneal implants, and the like, which can be configured to treat or ameliorate any of a variety of vision conditions in a particular patient based on their unique ocular characteristics or anatomy.

Figure 1:
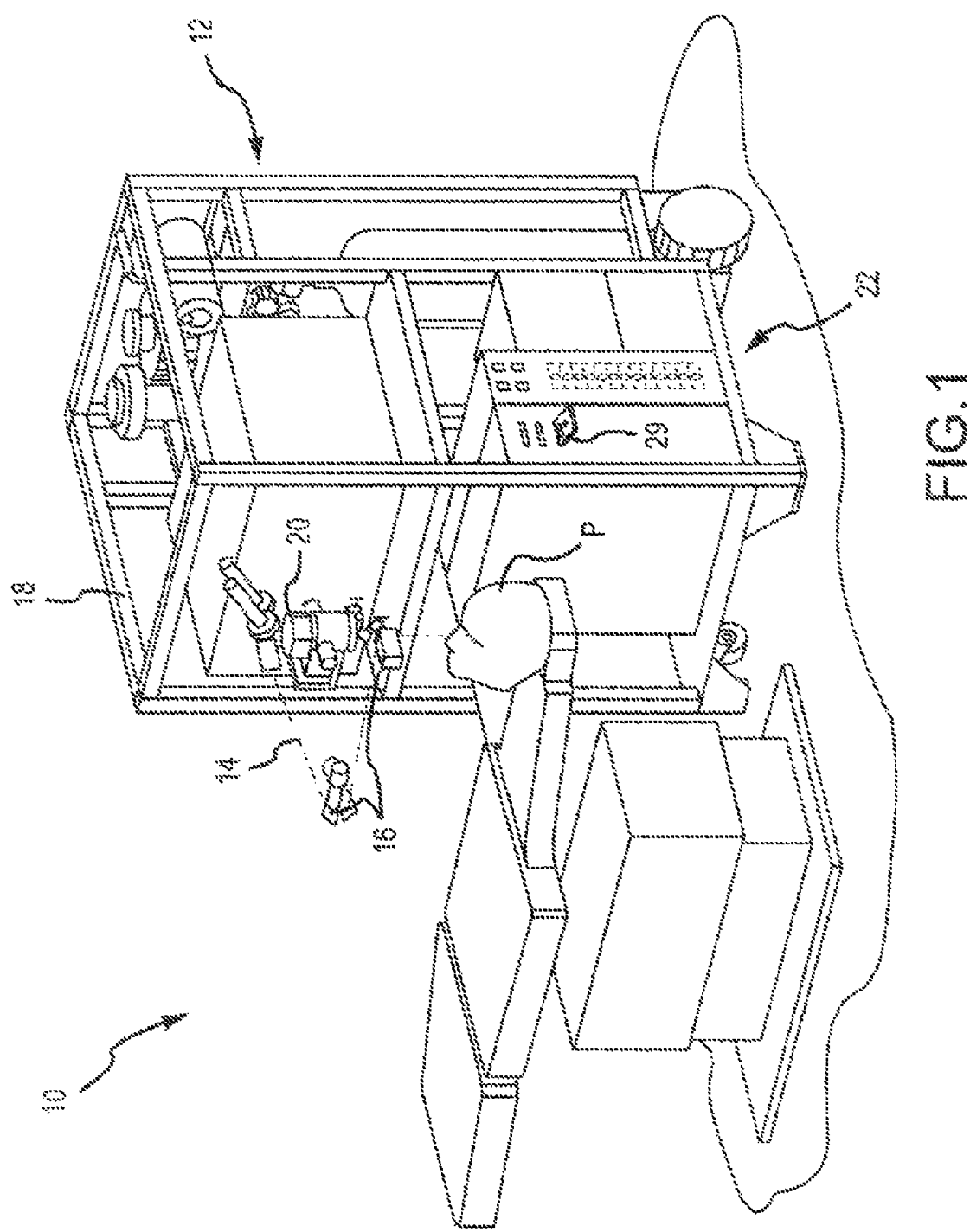
FIG. 1 illustrates a laser ablation system according to an embodiment of the present invention.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with an input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
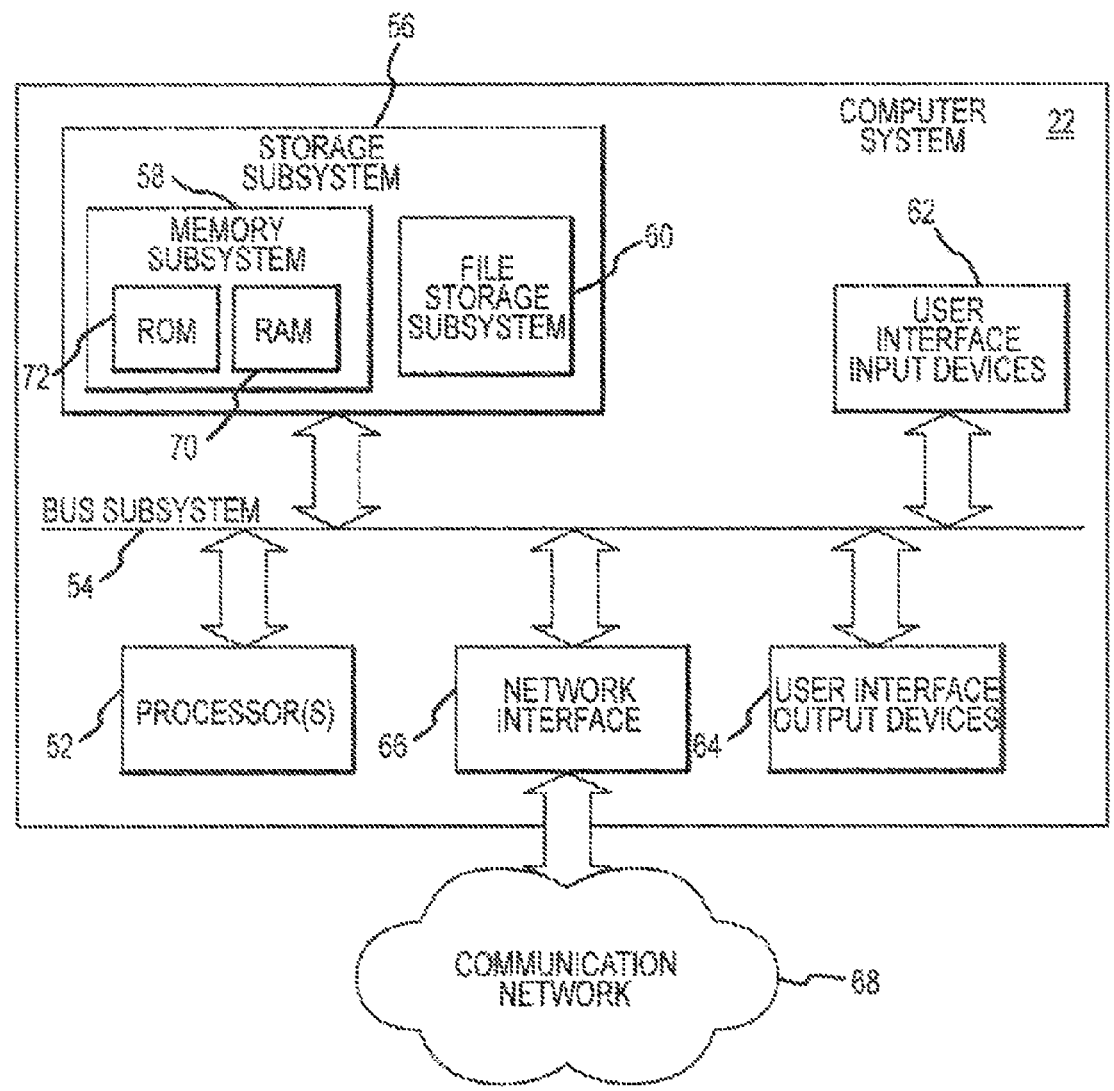
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
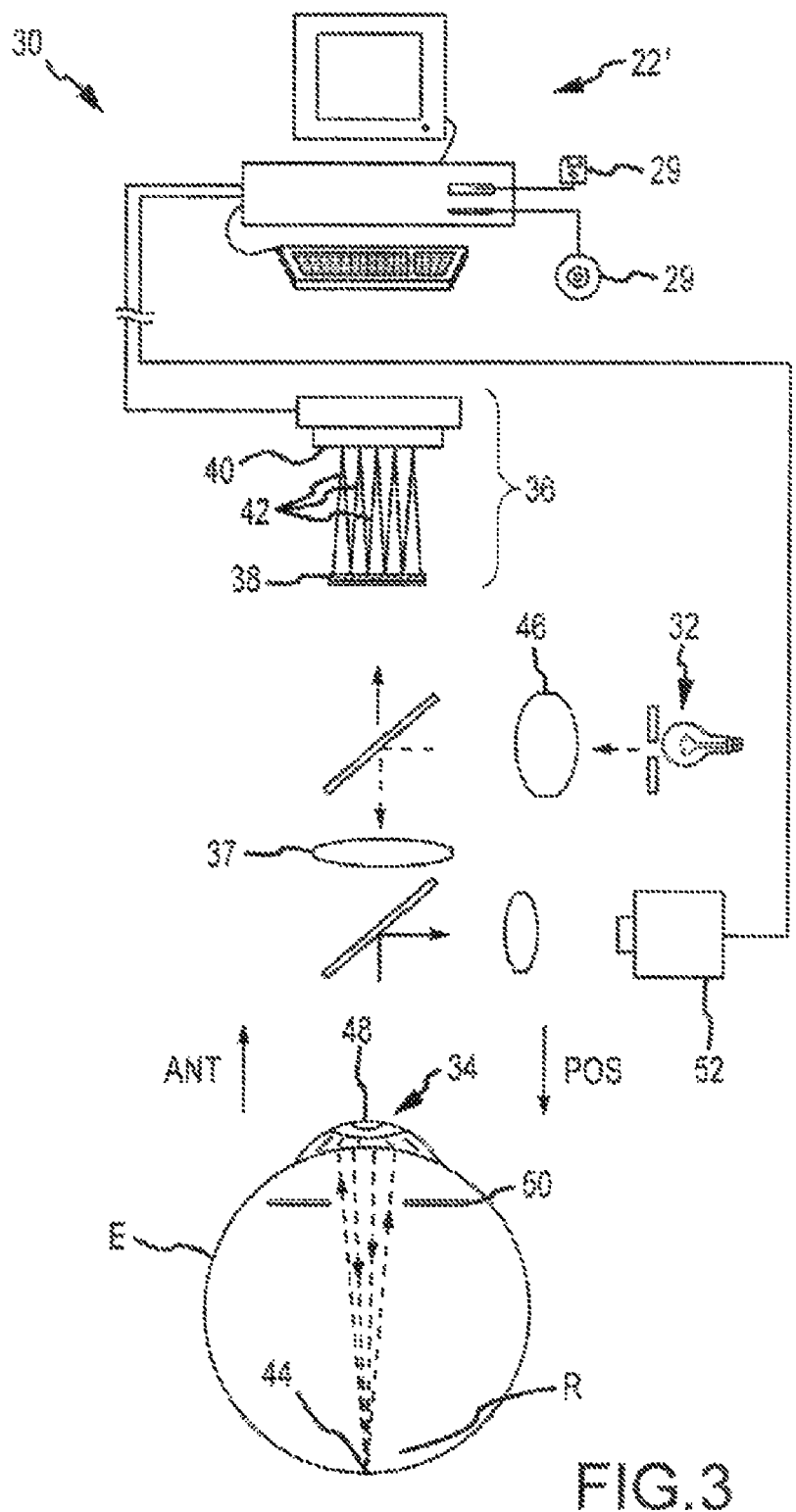
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
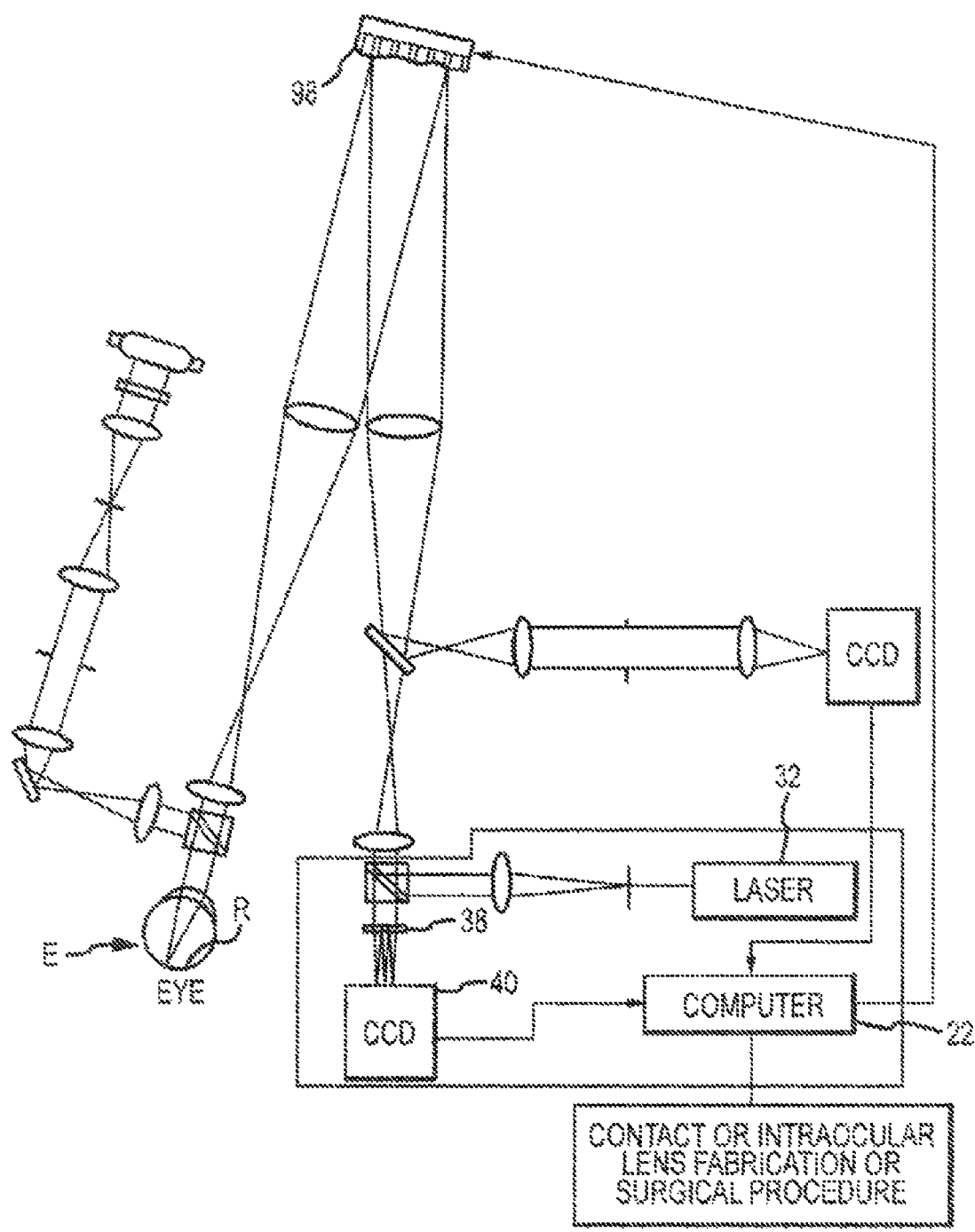
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from VISX, INCORPORATED of Santa Clara, Calif. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like.

In some embodiments, an aberrometer device can be used to measure whole eye spherical aberration (SA), and a topography device can be used to obtain a topography or spherical aberration of a cornea. Based on the whole eye SA and the cornea SA, the SA of the lens can be calculated. The change or difference in SA due to a natural lens or an accommodating IOL can be determined. Hence, accommodation can be measured. A wavefront may change as it propagates from one plane to another. Thus, topographic aberrations of the cornea can be represented at the exit pupil plane, and aberrations of the entire eye can be represented at the exit pupil plane. When deriving a difference between an ocular aberration and a corneal aberration, the difference may be represented at the exit pupil plane. When using the difference to determine an aberration of a natural lens or an accommodating IOL, the representation of the aberration may be translated, for example, to an IOL plane. Wavefront propagation conversions are discussed in co-pending and co-owned patent application Ser. No. 11/736,353 filed Apr. 17, 2007, the entire contents of which are hereby incorporated by reference for all purposes.

Embodiments of the present invention provide systems, methods, and devices for compensating voluntary accommodation of patients during wavefront measurements. These techniques can be used to improve the accuracy of the ocular aberration measurements and to improve the treatment of patients using laser vision correction treatments based on wavefront procedures. Such approaches can also be used to measure the residual accommodation of presbyopic patients and to customize treatment for such patients.

It is often difficult with some current techniques to achieve complete or desired lack of accommodation in a patient. For example, some have estimated that about 5% of the patient population presents unwanted accommodation during optical testing and treatment procedures. The techniques disclosed herein provide improved systems and methods that compel a patient's eye away from an accommodated state and toward an unaccommodated or deaccommodated state.

The amplitude of accommodation can be defined as the eye's ability to focus at near. A child's eye may be able to focus at about 2-3 inches, which corresponds to an amplitude of accommodation of about 10-30 diopters. In contrast, a 45 year old person may only be able to focus at about 20 inches, which corresponds to an amplitude of accommodation of about 2 diopters.

Figure 4:
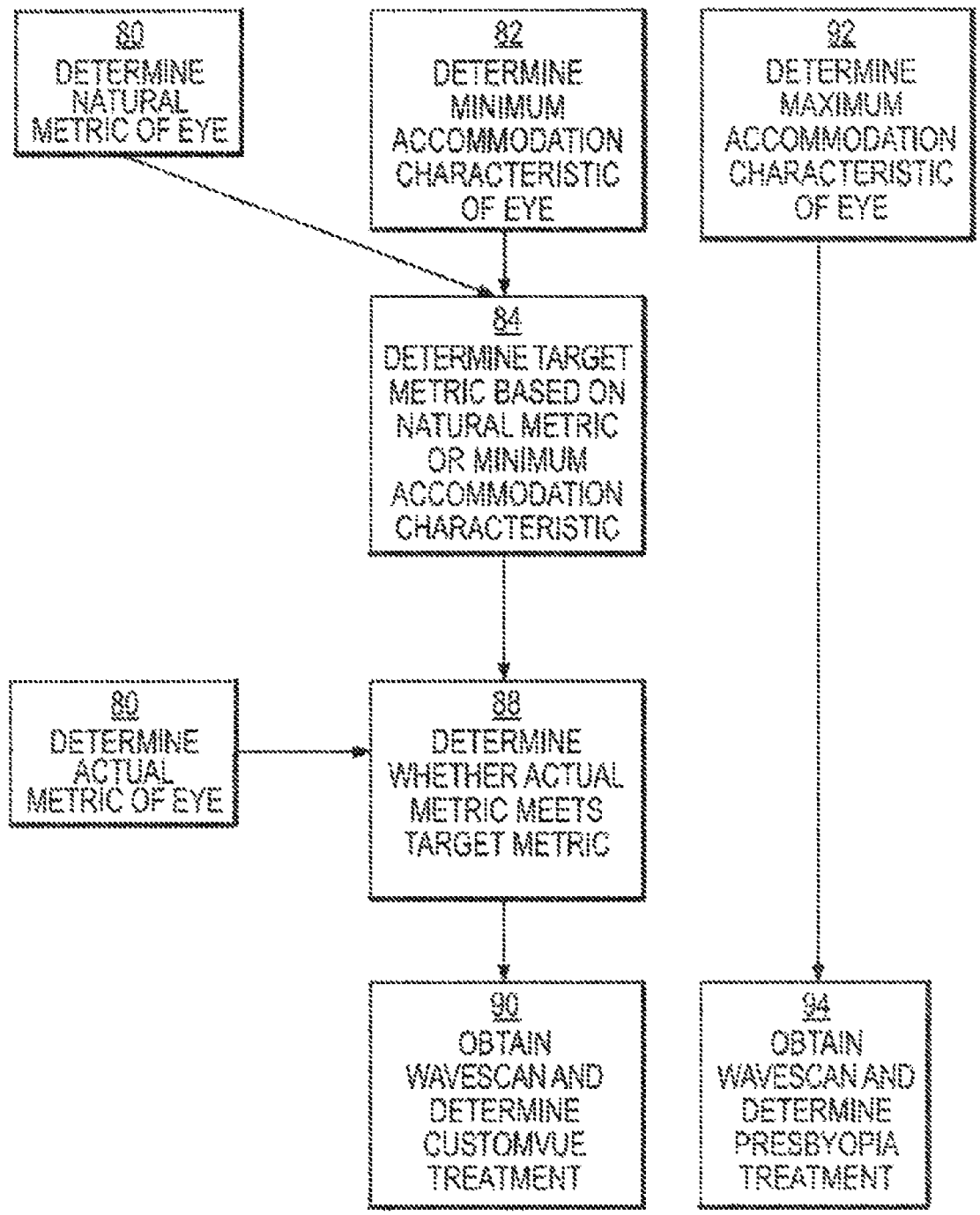
FIG. 4 schematically illustrates method embodiments of the present invention.

FIG. 4 schematically illustrates method embodiments of the present invention. These methods involve evaluating accommodation characteristics of a patient's eye, and determining corrective ocular treatments for the eye. Step 80 involves determining a natural metric of an eye. A natural metric of the eye can include, for example, the natural pupil size of the eye or the natural spherical aberration of the eye. Often, the term natural metric refers to a characteristic of the eye under natural conditions, in the absence of influences that may be present during diagnostic or testing procedures. For example, this term may indicate the pupil size of the eye when the patient is not subject to a particular diagnostic instrument. Accordingly, this term can be related to the status of the eye where instrument myopia is absent or reduced.

The patient eye metric can include a pupil size or a spherical aberration, as noted above. Patient eye metrics may also include coma or trefoil. More broadly, metrics suitable for use with embodiments of the present invention include low order aberrations, high order aberrations, primary or secondary astigmatism, primary or secondary coma, primary or secondary sphere, primary or secondary spherical aberration, pupil size, defocus, root mean square, high order root mean square with an error, and the like. Metrics may also encompass combinations, for example a metric may include coma and trefoil, which are third order aberrations. Similarly, a metric may include secondary astigmatism, spherical aberration, and quadrafoil, which are fourth order aberrations. Metric embodiments also encompass fifth order aberrations, sixth order aberrations, and the like. Such optical metrics may change as the accommodation of the eye increases or decreases. For example, the spherical aberration of the eye may increase as the eye changes toward a more accommodated state. The rate and magnitude of these metric changes often vary from patient to patient, and can even vary between eyes in a single patient.

Certain individuals within a population may present ocular characteristics which vary from the norm or from other individuals within the population. For example, it has been observed what within some populations, about 90 percent of the individuals present a natural spherical aberration that is positive, and about 10 percent of the individuals present a natural spherical aberration that is negative, when the eye is relaxed or unaccommodated. In some embodiments, metrics can be determined or evaluated with respect to ocular characteristics exhibited by a population or set of individuals. For example, a metric can be based on an average or mean pupil size of a group of individuals. Similarly, a metric can be based on an average or mean spherical aberration of a group of individuals. Relatedly, a diagnosis or treatment can be based on ocular characteristics of a population or subset thereof, in addition to or instead of a patient's particular ocular characteristic. In one embodiment, a patient treatment based on a mean value of spherical aberration from a population of individuals. In some cases, the mean value of spherical aberration from a population of individuals is determined based on a standardized pupil size. That is, within the population of individuals it is possible to characterize a spherical aberration characteristic with respect to a pupil size. Thus, a population mean spherical aberration can be associated with pupil size. A treatment for an individual patient can involve a pupil size normalization. Relatedly, it is possible to tailor a patient treatment based on a pupil size of the patient, and a mean value of spherical aberration from a population of individuals. For example, a treatment can be scaled based on the patient pupil size and the population mean.

When a patient eye fully or maximally unaccommodates during a wavefront measurement, the pupil size is relatively large. When the eye accommodates, the pupil constricts and often can be about 1.5 mm smaller than the unaccommodated pupil size. In some embodiments, a wavescan measurement can be performed under low light. When evaluating a patient's eye under low light, for example with an aberrometer, the pupil size is large or at or near its maximum. It may be desirable to capture or evaluation ocular aberrations of the patient's eye when the pupil is enlarged. If an examination is performed under intense light or when the pupil is constricted, there may be aberration information that is outside of the capture area that is missed. Evaluating the eye under low light can improve the likelihood of obtaining a reliable aberration representation for pupil dynamics when the pupil constricts.

Step 82 involves determining a minimum accommodation characteristic of the eye. The term minimum accommodation characteristic can include a characteristic of the eye that corresponds to the eye when in a minimally accommodated state. For example, a minimum accommodation characteristic can be a pupil size of the eye when the eye is minimally accommodated. This step can involve compelling a patient's eye toward an unaccommodated state, and concomitantly evaluating the accommodation status of the eye. A minimum accommodation characteristic reflects the state of the eye where further deaccommodation is difficult or no longer possible.

Step 84 includes determining a target metric based on the natural metric or the minimum accommodation characteristic. Step 86 includes determining the actual metric of the eye, and step 88 includes determining whether the actual metric meets the target metric. These steps involve a pre-testing or pre-examination approach whereby an accommodation status of the eye is evaluated prior to determining whether to proceed with a wavefront or other refractometer measurement. For example, it is possible to determine a pupil size of the eye that corresponds to the eye in a minimally accommodated state. The eye is then evaluated prior to a wavefront exam. If the pupil size of the eye is sufficiently different from the minimally accommodated pupil size, or sufficiently different from a target metric based on the minimally accommodated pupil size, then a decision can be made not to proceed with the wavefront measurement. If, however, the actual pupil size is sufficiently close to the minimally accommodated pupil size, or sufficiently close to a target metric based on the minimally accommodated pupil size, then a decision can be made to proceed with the wavefront measurement. Accordingly, step 90 involves obtaining a wavefront measurement with a WaveScan wavefront diagnostic system and determining an optical treatment, such as a CustomVue treatment, based on the measurement. Optionally, a procedure may include determining a maximum accommodation characteristic of a patient eye, as indicated by step 92. A presbyopia treatment can be determined based on the maximum accommodation characteristic of the eye, as indicated by step 94.

Figure 5:
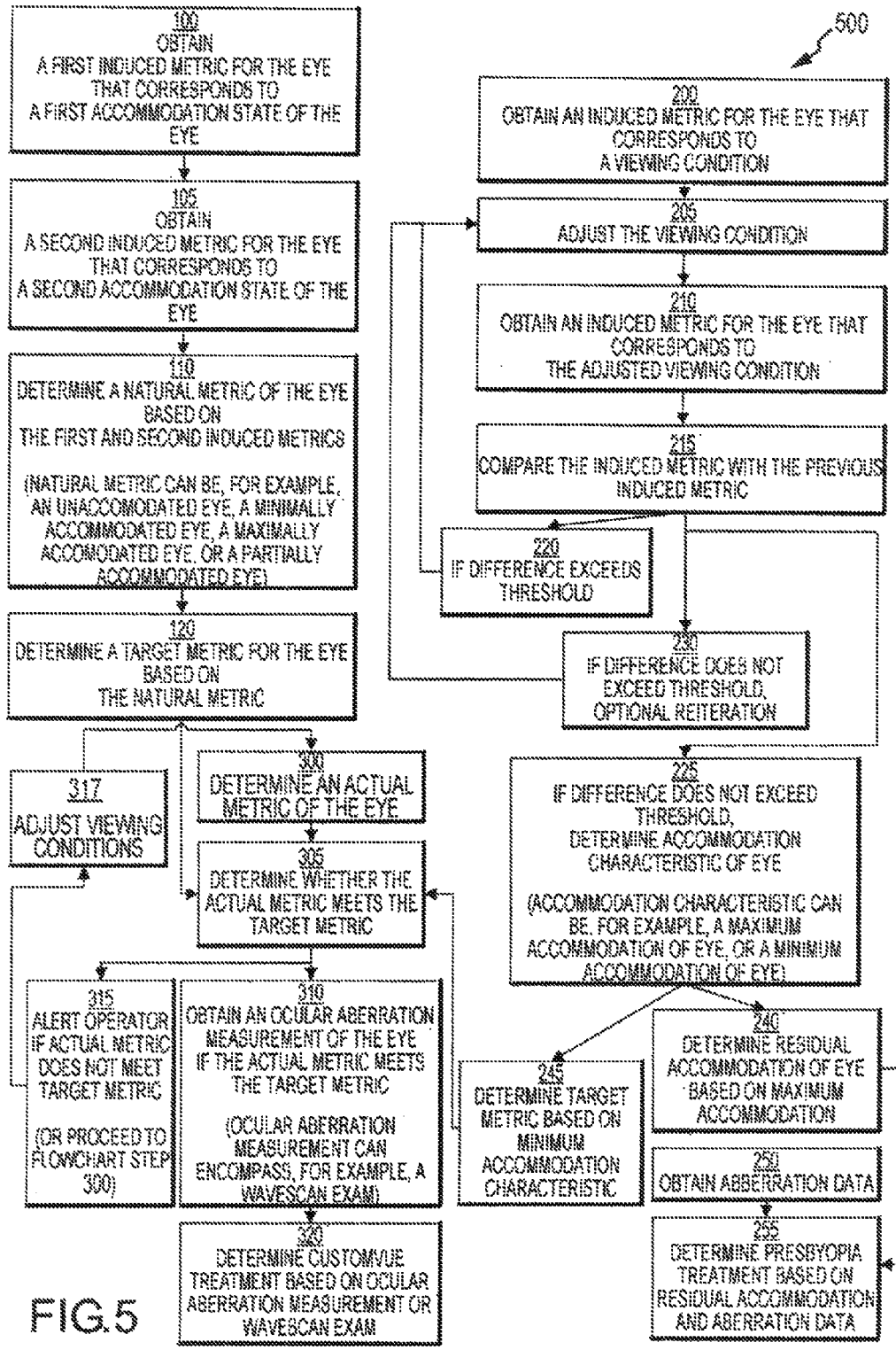
FIG. 5 depicts methods aspects of exemplary embodiments of the present invention.

FIG. 5 provides a detailed illustration of method embodiments of the present invention. In a first prong, method 500 includes obtaining a first induced metric for the eye that corresponds to a first accommodation state of the eye, as indicated by step 100. The first induced metric can include, for example, a pupil size of the eye or a spherical aberration of the eye. The pupil size can be measured by any of a variety of instruments, such as a video camera. The spherical aberration can be measured by an aberrometer such as a Hartmann-Shack device. Step 105 involves obtaining a second induced metric for the eye that corresponds to a second accommodation state of the eye. The second induced metric can include, for example, a pupil size of the eye or a spherical aberration of the eye.

This approach often involves physically pushing the eye toward a less accommodated state, or toward a more accommodated state, and monitoring the associated changes in the induced metric to determine whether or to what extent the eye is accommodated. In this way, it is possible to ascertain a model that predicts or determines the natural metric, which may correspond to an unaccommodated state of the eye. Any of a variety of stimuli or optical testing apparatuses can be used to compel accommodation changes in the pupil eye, including trial lenses, moving target, stimulated moving targets, and the like. A trial lens system may, for example, be used to simulate various target distances. Trial lenses can incorporate sphere, cylinder, or other properties. This technique often does not involve physically pushing the eye to the completely unaccommodated or accommodated state, however. Based on this approach it is possible to determine a relationship between the level of accommodation and the metric (e.g. pupil size, spherical aberrations, or vergence). In some cases, this relationship may be a linear relationship. In other cases, the relationship may be quadratic, logarithmic, exponential, or the like. Typically, the relationship is linear across a patient population.

Step 110 includes determining a natural metric of the eye based on the first and second induced metrics. The natural metric can be, for example, a pupil size or a spherical aberration for the eye when it is in an unaccommodated state. Similarly, the natural metric can be a pupil size or a spherical aberration for the eye when it is in a minimally accommodated state, a maximally accommodated state, or a partially accommodated state. As noted above, a natural metric refers to a characteristic of the eye under natural conditions, in the absence of influences that may be present during diagnostic or testing procedures. For example, the natural metric may refer to an eye characteristic in the absence of a stimulus or other optical testing apparatus. In some cases, this corresponds to a situation where there is no trial lens, or where the amount of the trial lens power does not provide a stimulus or induce an unwanted amount of defocus. Similarly, the intensity of the ambient light can be adjusted or maintained so as to not provide a stimulus. Step 120 encompasses determining a target metric for the eye based on the natural metric. The target metric can be, for example, a target pupil size or a target spherical aberration of the eye. In a second prong, method 500 includes obtaining an induced metric for the eye that corresponds to a viewing condition, as indicated by step 200. The method can also include adjusting the viewing condition, as shown by step 205. The viewing condition can be adjusted, for example, by adjusting a trial lens, by adjusting a target distance, by adjusting a simulated target distance, and the like. Step 210 includes obtaining an induced metric for the eye that corresponds to the adjusted viewing condition. These induced metrics can include, for example, a pupil size or a spherical aberration of the eye of the patient.

In some cases, this technique can include subjecting the patient to a series of accommodation tasks of varying diopters. For example, an accommodation task protocol may involve adjusting the viewing condition so as to subject the patient to sequential diopters of ½ D, ¼ D, ½ D, ¾ D, 1 D, ¾ D, ½ D, ¼ D, 0 D, and so on. Again, the viewing condition can be adjusted by adjusting a trial lens system or by adjusting a target distance. The viewing conditions can be varied in any way desired. In some cases, the viewing conditions may include a protocol providing sequential diopters in 0.1 D increments. Parameters of the method can be adjusted according to the desired or required degree of accuracy.

A presbyopia application may involve adjusting the viewing conditions so as to provide a continually increasing diopter protocol to the patient. Such a protocol may include, for example, sequential diopters of ¼ D, ½ D, ¾ D, 1 D, 1¼ D, 1½ D, and so on. As noted previously, the protocol can be metered in 0.1 increments. Thus, step 200 may involve obtaining an induced pupil size for the eye that corresponds to a ¼ D viewing condition, step 205 may include adjusting a trial lens or a target distance to change the viewing condition from ¼ D to ½ D, and step 210 may include obtaining an induced pupil size for the eye that corresponds to the ½ D viewing condition. In an exemplary embodiment, the viewing condition can be adjusted until the patient's pupil size, or spherical aberration, or some other metric, ceases to change or meets a certain threshold or value.

Similarly, the viewing condition can be changed until the difference between certain induced metrics meets or exceeds a certain threshold or value Accordingly, step 215 includes comparing the induced metric of step 210 with the previous induced metric of step 200. In the case of a pupil size measurement, if the difference between a first viewing condition pupil size and a second viewing condition pupil size is sufficiently large, then the method may involve reiterating steps 205, 210, and 215. If the difference between the previous viewing condition induced metric and the subsequent viewing condition induced metric is not sufficiently large or does not meet or exceed a certain threshold, then method 500 can include determining an accommodation characteristic of the eye as indicated by step 225. The accommodation characteristic can encompass, for example, a maximum accommodation of the eye or a minimum accommodation of the eye. In some cases, the viewing condition is adjusted, and the induced metric is monitored, until the induced metric no longer changes even under continued adjustments in the viewing condition. In some cases, the induced metric can be modulated or effected by changing the distance of the viewing target. Relatedly, a viewing condition can include a vergence testing or treatment parameter, which can be varied during examination or treatment. Similar viewing conditions are discussed in co-pending and commonly owned U.S. patent application Ser. Nos. 10/872,331 filed Jun. 17, 2004, and 11/156,257 filed Jun. 17, 2005, the contents of which are incorporated herein by reference. In some embodiments, it may be desirable to evaluate or treat an eye under a vergence condition that is zero or close to zero, or that is at some other value. A vergence can be based on a reciprocal of a target distance. Based on such procedures, it is possible to determine whether the eye is minimally accommodated or maximally accommodated. The method may involve determining whether the corresponding induced metrics, for example pupil size or spherical aberration, have reached a certain expected value or level. In some cases, if the difference between the previous viewing condition induced metric and the subsequent viewing condition induced metric is not sufficiently large or does not meet or exceed a certain threshold, then method 500 can optionally include iterating steps 205, 210, and 215 as indicated by step 220.

In the case of a maximally accommodated eye, the method may include adjusting the trial lens to sequentially increase (e.g. in 0.1 D or 0.25 D increments) the diopter for the viewing condition, and using a video camera to track and measure the corresponding pupil size changes. At some point, the pupil size ceases to change, even as the viewing condition continues to be adjusted. In this way, the method encompasses forcing the eye to the limit to determine a forced maximum accommodation. In a preferred embodiment, ambient light is maintained at a constant during this procedure, as changes in ambient light may have an effect on pupil size.

In the case of a minimally accommodated eye (or a maximally unaccommodated eye), the method may include adjusting the trial lens to sequentially decrease (e.g. in 0.1 D or 0.25 D increments) the diopter for the viewing condition, and using a video camera to track and measure the corresponding pupil size changes. Typically, decreasing power viewing conditions are associated with increasing pupil size dimensions. At some point or threshold, the pupil size reaches a maximum level and does not increase, even as the viewing condition continues to be adjusted. This can be the stage where accommodation is completely or maximally relaxed. The adjustments of the viewing conditions and the measurement of the induced metrics can be automated by software.

As an illustrative example, it is helpful to consider subjecting a patient to a variety of viewing conditions so as to determine an accommodation characteristic of the patient's eye, such as a maximum accommodation or a minimum accommodation of the eye. For example, the viewing condition can be adjusted so as to subject the patient to a series of increasing diopters values, and the induced metric ceases to change when the viewing condition reaches 2 D, then it may be possible to determine that the patient has 2 D of residual accommodation. When determining a minimum accommodation of the eye, the viewing conditions typically include a progression toward decreasing diopters. Relatedly, when determining a maximum accommodation of the eye, the viewing conditions typically include a progression toward increasing diopters.

Presbyopia Treatment

Method 500 can also include determining a residual accommodation of an eye based on characteristics of the eye in a maximally accommodated or highly accommodated state as indicated by step 240. Residual accommodation can be related to the trial lens power or the target distance. Residual accommodation can be based on a power that is determined by the reciprocal of the target distance. As a person ages, the ability to accommodate typically diminishes. Residual accommodation reflects a measure of the accommodative capacity that a patient retains. Thus, a patient having a lower degree of residual accommodation exhibits more severe presbyopia, whereas a patient having a higher amount of residual accommodation exhibits less severe presbyopia. For example, an eye having one diopter of residual accommodation may allow a patient to image with good acuity anywhere throughout a one-diopter target distance range. Residual accommodation is also discussed in U.S. patent application Ser. No. 11/134,630 filed May 19, 2005, the entire content of which is incorporated herein by reference. It may be desirable to include the amount of residual accommodation in the design of a presbyopic treatment so the patient may achieve an optimal outcome. The method may also include a screening step, whereby a determination is made whether to treat the patient based on the residual accommodation measurement. In many cases, it may be easier or more desirable to optimize a treatment shape for a patient having a higher residual accommodation. Embodiments of the present invention encompass screening systems and methods for choosing or selecting IOLs. For example, an optical apparatus can include an IOL or accommodating IOL placed in the optical path, and the IOL or accommodating IOL can be used as part of the optical element in the optical bench. Subjective testing can be performed for screening purposes, and this can be done prior to surgery or treatment.

As shown by steps 250 and 255, the method may also include obtaining aberration data, for example with a WaveScan device or the like, and determining a presbyopia treatment based on the residual accommodation and the aberration data. Embodiments of the present invention encompass screening systems and methods that determine whether to proceed with a corneal ablation treatment based on the residual accommodation of the patient. For example, if the residual accommodation of the patient as determined in step 240 is sufficiently large, the technique may involve proceeding with an ablative treatment. Conversely, if the residual accommodation is sufficiently small, the technique may involve refraining from administering an ablative treatment to the patient. In some cases, the threshold residual accommodation is about 0.5 Diopters, whereby if the patient has a residual accommodation greater than about 0.5 D, an ablative treatment is administered to the patient, but if the residual accommodation is less than about 0.5 D then the patient is provided with a multifocal IOL. Techniques may involve aspects of residual accommodation and threshold residual accommodation which are discussed in co-pending and co-owned U.S. patent application Ser. No. 11/134,630, the contents of which are incorporated herein by reference.

In this way, the residual accommodation can be used to determine an appropriate or desired treatment modality for a presbyopic patient. For example, in presbyopes having a larger amount of residual accommodation, it may be desirable to administer a corneal reshaping treatment. In presbyopes having a smaller amount of residual accommodation, it may be desirable to treat the patient with a multifocal IOL. Thus, the determination can be made based on the residual accommodation of the patient, and independently of the age of the patient.

In some cases, when designing a presbyopia prescription shape based on the residual accommodation, it may be desirable to design the shape so as to maintain a substantial or maximal degree of distance vision. However, there is often a trade off as presbyopia correction typically involves a compromise between optimal near vision and optimal distance vision. For example, in an older patient having less residual accommodation, it may be desirable to administer a treatment that includes a slightly higher spherical aberration, thus providing an increase in near power (near vision) but a decrease in far power (distance vision). In a patient having more residual accommodation, it may be desirable to administer a treatment that includes a less aggressive aspheric component, thus providing less of an increase in near power and less of a decrease in far power. Often, the process of designing a prescription shape includes decisions regarding the management of simultaneous near and far vision, as well as whether the near vision meets or approaches a desired threshold or standard.

CustomVue Procedure

The WaveScan wavefront diagnostic system measures aberrations of the ocular optical system. Based on wavefront measurements, the system generates graphic displays of those aberrations, generates mathematical models of the aberrations, and transmits aberration data for use by a VISX laser eye surgery system. In addition to standard optical defects such as myopia, hyperopia, and cylindrical astigmatism, this diagnostic tool provides objective measurements of higher-order aberrations of the eye. VISX laser eye surgery systems can direct ablative laser energy from an excimer laser toward a cornea of a patient. A processor of the VISX laser system can direct a pattern of the ablative energy toward the corneal tissue so as to alter the shape of the cornea, effectively changing the shape of the corneal lens. The corneal stroma is selectively ablated by the laser energy so as to resculpt the cornea, modifying the refraction provided by the cornea itself. In a CustomVue treatment procedure, the pattern of ablative energy is derived from the wavefront aberration data measured by the WaveScan wavefront diagnostic system so as to correct low and high-order aberrations of the eye, thereby providing a corrected visual performance that often exceeds that available through standard corrections such as off-the-shelf spectacles or contacts.

Method 500 can also include determining a target metric based on a minimum accommodation characteristic of an eye, as indicated by step 245. This approach includes pushing the eye to or toward an unaccommodated or minimally accommodated state. For example, the approach may involve asking or forcing the patient to accommodate, via a trial lens system or a changing target distance protocol, so as to induce sphere in the eye. Then, the distance between the patient and the target can be decreased, or the trial lens system can be adjusted toward decreasing powers, so as to reduce the plus lens. Eventually the patient will approach or reach an unaccommodated or minimally accommodated state. The target metric can be calculated based on the unaccommodated or minimally accommodated state of the eye.

As indicated in step 300, the method may also include determining an actual metric of the eye. For example, a video camera can be used to determine the actual, and in some cases real time, pupil size or dimension of the eye. Similarly, a Hartmann-Shack device can be used to determine an actual spherical aberration of the eye. Step 305 includes determining whether or to what degree the actual metric meets or approaches the target metric. This step may involve determining whether the eye is unaccommodated or minimally accommodated. In this way, an operator can ensure that the examined eye is unaccommodated, minimally accommodated, or the like, which may indicate that instrument myopia is no longer induced, and that there is no vergence. The determination can be based on aberration data, the pupil size, or some other data. This technique is helpful in decreasing or eliminating error in situations where the patient's eye is continuing to accommodate somewhat. In certain CustomVue treatments, when the eye accommodates the reported wavescan is not accurate for sphere or spherical aberration, and it may be difficult to determine whether the eye is unaccommodated as desired. In some cases, the determination of an unaccommodated state may be difficult because of microaccommodation and the tear film fluctuations. Embodiments of the present invention provide a systematic way of compelling the patient toward an unaccommodated state.

According to embodiments of the present invention, it is therefore possible to monitor the actual metric (e.g. pupil size) to determine whether or to what extent the eye of the patient is approaching an unaccommodated or minimally accommodated state. If the actual metric does not meet the target metric, the method may include adjusting the viewing condition so as to push the eye toward a more accommodated state or toward a less accommodated state. This can be accomplished with a trial lens system, a moving target, a simulated moving target, and the like. The method may also include providing a signal to the operator indicating whether a maximally or highly unaccommodated state is reached or maintained. Further, the method may include making a decision whether to proceed with an ocular aberration measurement or not, based on whether or to what degree the actual metric approaches or meets the target metric, as indicated by step 310. As noted previously, the target metric can be determined by step 120 (based on natural metric) or by step 245 (based on minimum accommodation characteristic).

The ocular aberration measurement of step 310 may include a wavescan exam. For example, if the actual accommodation state of the eye meets the target accommodation state, the method proceeds with a full wavefront scan. Typically, the trial lens is removed from the optical path prior to taking the aberration measurement. Embodiments of the present invention encompass techniques that involve compelling the eye toward a deaccommodated state, and measuring a wavefront of the eye when the eye is in a minimally accommodated state.

In this way, it is possible to ensure that the accommodation state of the eye is known when the ocular aberration measurement is taken. For example, it may be desirable to ensure that the eye is unaccommodated or substantially unaccommodated when a wavescan exam is performed. In some cases, it may be possible to proceed directly to ocular aberration measurement of step 310 after determining that threshold is not exceeded in step 225.

As shown in step 315, the method may include alerting a system operator if the actual metric does not meet the target metric. For example, the patient may not be sufficiently deaccommodated. Optionally, the method may include adjusting the viewing condition in an attempt to change the actual metric of the eye, as indicated by step 317. The method may then include returning to step 300 to determine the actual metric of the eye.

Thus, embodiments of the present invention provide a series of pre-examination measurements, whereby a method may encompass performing a series of preliminary validation steps prior to the aberration measurement. Typically, these tests involve induced vergence or induced myopia. In order to ascertain the desired parameters, such as the state of a minimally accommodated eye, the method may involve pushing the eye toward a less accommodated state or a more accommodated state. When the pretesting is complete, the testing optics can be removed and the aberration measurement can proceed. In a typical scenario, prior to a wavefront exam a patient is subjected to a trial lens protocol that pushes the eye from a more accommodated state toward a less accommodated state. If the patient eye does not reach a desired level of unaccommodation, the method may include providing a warning message to the system operator that the eye is not sufficiently unaccommodated. If the patient eye reaches the desired level of unaccommodation, the method may include proceeding with a wavescan exam. The method may or may not include removing the optical testing apparatus from the optical path prior to the aberration measurement. For example, when evaluating a pupil size metric, it may be possible to leave a trial lens in the optical path. Conversely, when evaluating a spherical aberration metric, it is often desirable to remove a trial lens from the optical path prior to performing the ocular aberration measurement.

In some embodiments, a method may include measuring a plurality of spherical aberrations to determine an accommodation profile of an eye. In this way, it is possible to determine an ocular aberration relative to a spherical aberration structure.

Figure 6A:
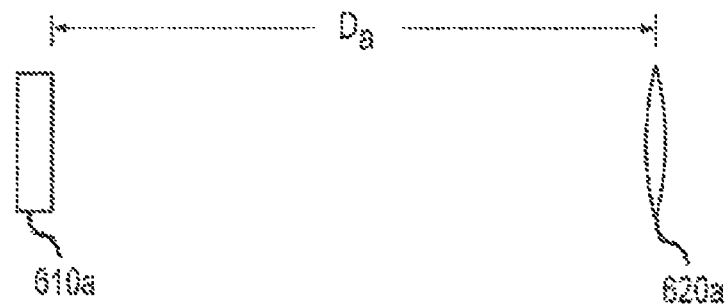
FIGS. 6A-6C illustrate the effects of changing focal distance on a patient's lens, according to embodiments of the present invention.
Figure 6B:
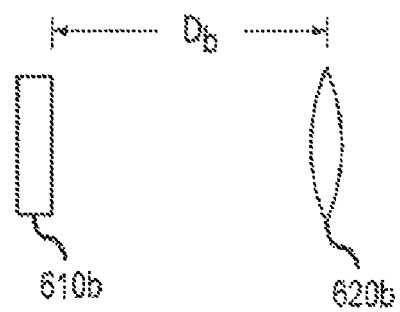
Figure 6C:
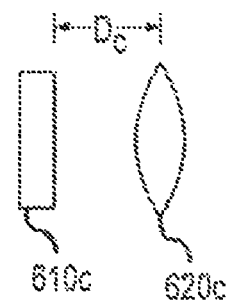

FIGS. 6A-6C illustrate the effects of changing focal distance on a patient's lens. In some cases, a large pupil size may be beneficial in capturing such information. SA measurements may be used to characterize or predict the hardness of a nucleus. It is possible to derive a spherical aberration of a nucleus based on a total ocular spherical aberration and a topography measurement of spherical aberration of a cornea. Embodiments provided herein encompass models which reflect a person's age, the hardness of the nucleus, and the spherical aberration. For example, it is possible to build a model where as a person ages, a nucleus becomes harder, and spherical aberration increases. Models may be constructed from population studies, to support predictions of nucleus characteristics, such as hardness, based on spherical aberration measurements. A human crystalline lens consists of material having a gradient index of refraction. Spherical aberration and other aberration parameters can change during accommodation, as well as during mini-accommodation or micro-accommodation, because of the corresponding change in shape of the crystalline lens. Thus, accommodation involves a change in lens shape accompanied by a change in optical aberrations. For example, a lens in a less accommodated state can be flatter, having a lower diopter and higher focal length. In contrast, a lens in a more accommodated state can be more round, having a higher diopter and a smaller focal length. In an unaccommodated state, the spherical aberration of the eye or lens is relatively small. When the eye accommodates, the shape of the lens becomes more round or bulging, thus increasing the amount of spherical aberration. Typically, as a person ages the capacity for the eye to accommodate diminishes. It has also been observed that the pupil constricts as the eye accommodates. However, in many cases the amount of pupil constriction is independent of the patient's age. FIG. 6A shows a target 610a at or near optical infinity, with a high focal distance $D_a$. Accordingly, lens 620b is relatively flat, has a low diopter, and is in a more relaxed accommodation state. FIG. 6B shows a target 610b that is closer to the eye, with a medium focal distance $D_b$. Accordingly, lens 620b is somewhat bulging. FIG. 6C shows a target 610c that is very close to the eye, with a short focal distance $D_c$. Accordingly, lens 620c has a highly bulging shape. The sphere and spherical aberration components typically change in these situations. For example, the sphere and spherical aberration can be relatively small in FIG. 6A, intermediate in FIG. 6B, and relatively large in FIG. 6C. As FIGS. 6A-6C illustrate, as a target moves closer to the eye, the lens adopts a greater curvature so as to keep the target in focus. In a presbyopic patient, the ability to transition from a flatter lens to a bulging lens is diminished. Thus, the lens remains flatter, even when the patient is trying to gaze at a near distance, for example when reading a newspaper.

Figure 7A:
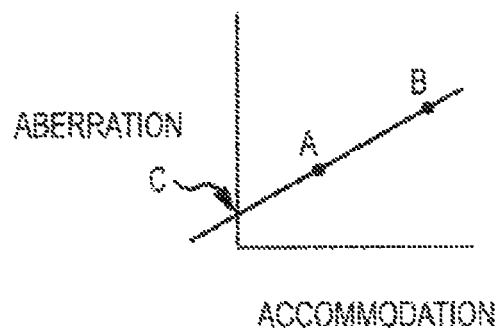
FIGS. 7A-7E illustrate relationships involving ocular characteristics of an eye according to embodiments of the present invention.

In many optical procedures where the patient is subject to the influence of optical testing machinery, it may be difficult or impossible for the patient to completely relax the lens of the eye. Accordingly, there is often some accommodation, which may be referred to as instrument myopia. This instrument myopia may be present even when the patient is trying to suppress the accommodation. Hence, optical measurements that are designed to reflect the status of the eye may include some amount of accommodation. It is useful to characterize the relationship between an optical measurement and the accommodation of the eye. FIG. 7A graphically illustrates a relationship between a spherical aberration (y axis) and an accommodation state (x axis) of the eye. An exemplary procedure may include monitoring the patient's wavefront scan under a variety of different viewing conditions, for example a series of accommodation tasks. A metric such as spherical aberration can be determined from the wavefront, and synchronized or correlated with the accommodation tasks. As shown here, as the eye becomes more accommodated in response to changing viewing conditions. The increase or change in accommodation can be in response to, for example, a stimulus such as an optical testing apparatus, which induces the amount of spherical aberration in the eye to increase or otherwise change. A first induced spherical aberration can be represented by point A, and a second induced spherical aberration can be represented by B.

In one illustrative example, a patient accommodates to a target and a wavefront measurement is taken. The target is then moved, and another wavefront measurement is taken. This can be driven by known change in sphere. For example, a target distance can be moved from 1 meter to 2 meters, or from 1 meters to 0.5 meters, or the like. Similarly, a target distance can be fixed and a trial lens can be manipulated by changing the sphere. This can provide a similar effect to changing the target distance or vergence viewing condition. By analyzing the wavefront readings, it is possible to correlate a change in ocular aberration with the state of accommodation in the eye. A wavefront measurement or metric corresponding to the unaccommodated eye (e.g. zero accommodation) can be extrapolated or determined based on this correlation.

A relationship between spherical aberration and accommodation can be established based on the induced metrics, and the relationship can be used to determine or predict metric values at various levels of accommodation. For example, it is possible to predict or extrapolate the spherical aberration at point C, which corresponds to the eye in the unaccommodated state. Zero accommodation is analogous to eye gaze at infinity. A similar approach can be used to predict a patient's pupil size or dimension for a given amount of accommodation. Related methods include qualifying a certain wavefront measurement out of several wavefront measurements.

Figure 7B:
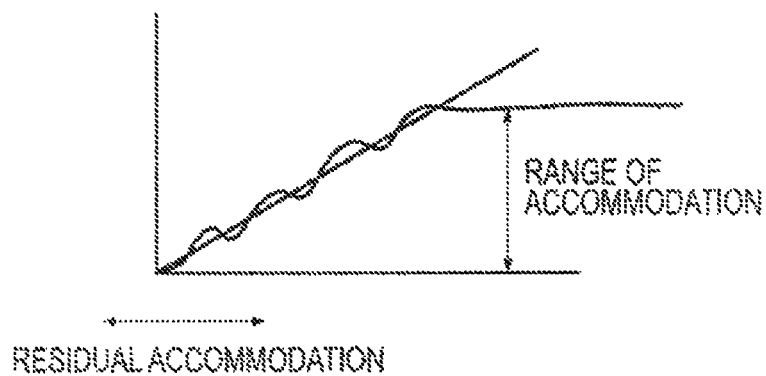

FIG. 7B graphically illustrates a relationship involving residual accommodation and range of accommodation.

A residual range of accommodation can be quantified or configured, and algorithms can derive a presbyopia shape.

Parameters for design include the Residual Range of Accommodation, which may be particularly useful for designing a presbyopia treatment. Pupil dynamic parameters can also be used in the design of a presbyopia treatment.

Based on data from the relationship shown in FIG. 7B, it is possible to determine an optimal accommodation pattern for a specific patient, and therefore it is possible to determine an optimal vision correction treatment for the patient. In some cases, the vision treatment encompasses a treatment for presbyopia. For example, some patients may benefit from a reduced amount of add in the presbyopic correction. As depicted in FIG. 7B, residual accommodation is represented by the portion where the line levels off horizontally, which corresponds to a maximally accommodated eye.

Figure 7C:
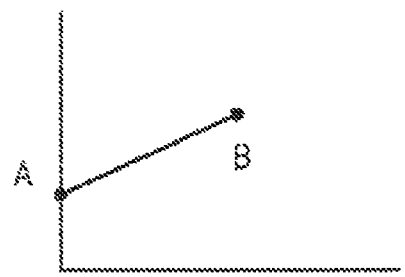

FIG. 7C graphically illustrates a relationship involving optical characteristics of an eye. The point A represents a typical or normal patient. Point B represents an older patient that has presbyopia. A typical wavefront aberration includes contributing factors such as a lenticular aberration (or lens aberration) and a corneal aberration. Often, however, it is difficult to determine from a wavefront scan which wavefront aberrations derive from lenticular aberrations and which derive from corneal aberrations. It may be desirable to characterize the contributing factors of the wavefront. One approach involves the assumption that the corneal aberrations are known, and that the lenticular aberrations vary in response to changing viewing conditions or stimuli. Hence, it is possible to evaluate changes in the wavefront that occur in response to the viewing conditions, and attribute these changes to lenticular aberrations. Based on this approach, it is possible to determine what factors contribute to a wavefront aberration.

Advantageously, it has been discovered that through-focus measurements of an ocular wavefront can be used to derive accommodation-free refraction, and thus lenticular (lens) contribution to ocular wavefront can be determined, for example based on a combination of topographic data and ocular wavefront measurement data, it is possible to derive a lenticular contribution.

Figure 7D:
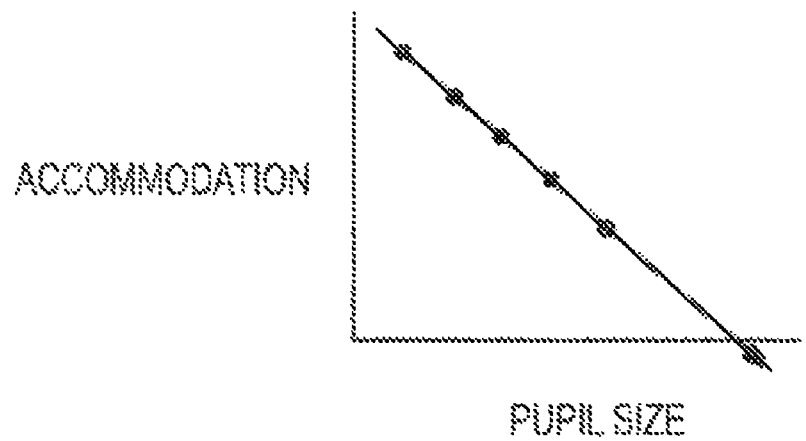

FIG. 7D graphically illustrates a relationship between an accommodation state (y axis) and a pupil size or dimension (x axis) of the eye. An exemplary procedure may include monitoring the patient's eye under a variety of different viewing conditions. The viewing conditions may encompass a series of accommodation tasks. The method may also include correlating the pupil dimension metric with the accommodation status. As shown here, an increase in pupil dimension is correlated with a decrease in the level of accommodation in the eye. A relationship between accommodation and pupil size can be established based on these values. It is therefore possible to extrapolate to determine a pupil size that corresponds to a zero accommodation state of the eye. Often, determination of an accommodation-free pupil size is achieved under consistent, calibrated ambient lighting. Thus, lighting can be calibrated for pupil size purposes. Based on the data provided by FIG. 7D, it is possible to determine an accommodation value for a particular pupil size.

As shown in FIG. 7D, a maximum accommodation state of the eye can correspond to a minimum pupil size of the eye, and this can be determined by adjusting an accommodation target or stimulus. Based on this data, it is possible to calculate the residual accommodation, which can be described as the amount of accommodation that remains in the eye. The residual accommodation can be calculated based on a distance between the eye and the target. Patients having more severe presbyopia have less residual accommodation Patients with milder presbyopia have more residual accommodation. Pupil size thus can be an independent indicator of accommodation.

Figure 7E:
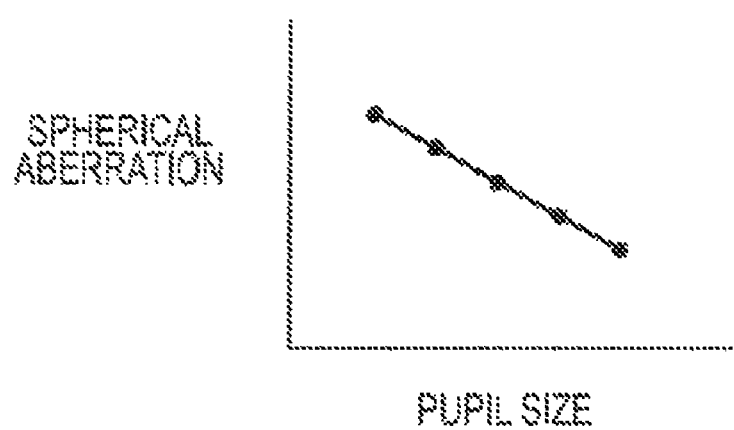

FIG. 7E graphically illustrates a relationship between a spherical aberration (y axis) and a pupil size or dimension (x axis) of the eye. An exemplary procedure may include monitoring the patient's pupil size under a variety of different viewing conditions, for example a series of accommodation tasks. A metric such as pupil diameter can be determined by a video camera, and synchronized or correlated with the spherical aberration, which may be determined based on a wavefront scan. As shown here, an increased pupil size correlates with a decreased spherical aberration. A relationship between spherical aberration and pupil size can be established based on these values.

Figure 8:
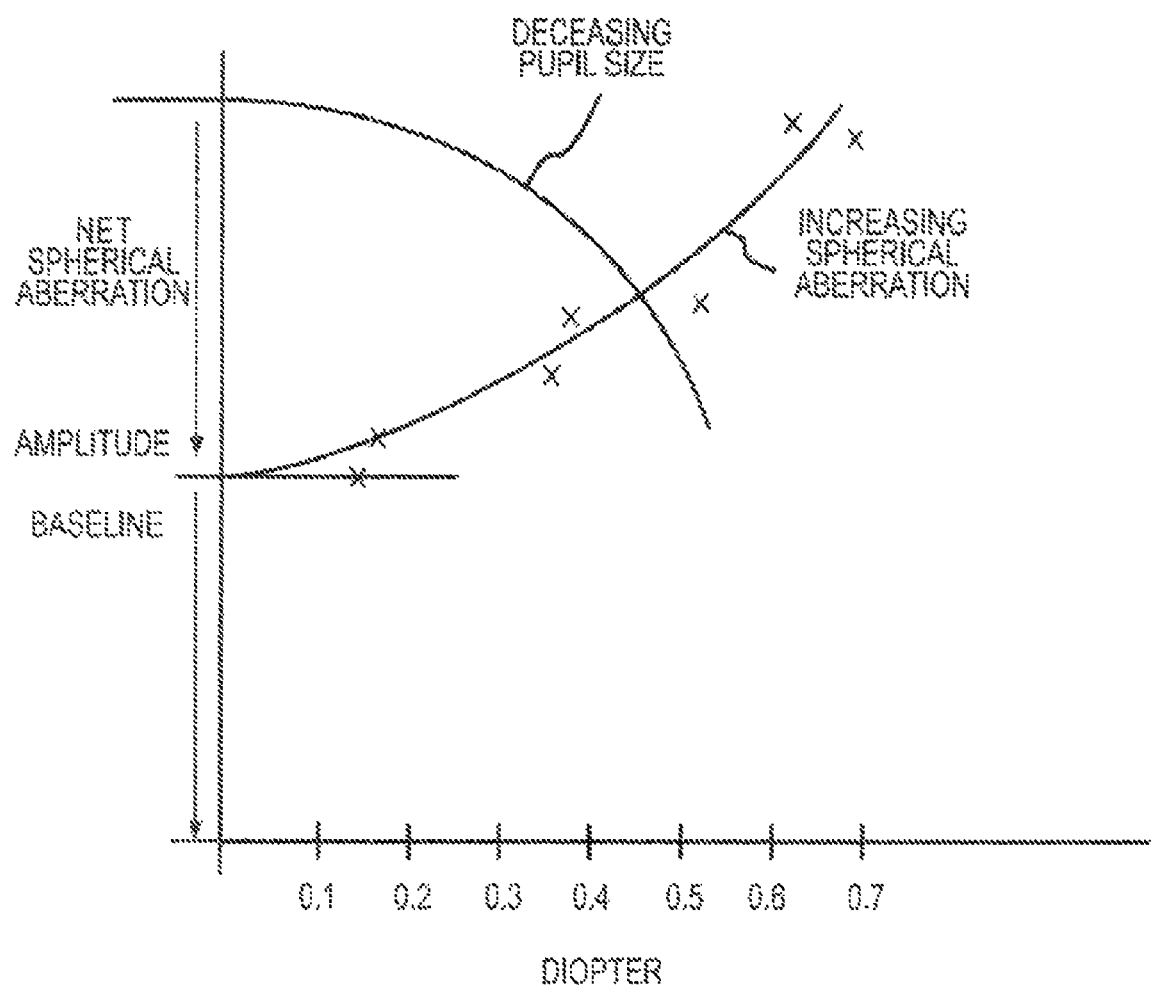
FIG. 8 depicts relationships between accommodation, pupil size, and net spherical aberration according to embodiments of the present invention.

FIG. 8 depicts relationships between accommodation, pupil size, and net spherical aberration according to embodiments of the present invention. In an exemplary technique, a series of accommodations tasks is given to a patient, and a corresponding series of wavefront measurements is taken. As the accommodation response results in a change of the eye lens, characteristic ocular aberrations such as sphere (defocus), spherical aberration (shape change), and coma (lens decentration) can be correlated with different values of the wavefront bias or spherical bias due to instrument myopia. Aberrations can also be correlated with different values of pupil size. These metrics can be used to determine a prescription for an optimal IOL, an accommodating IOL, and the like, or for the derivation of design parameters for a multi-focal presbyopic correction on the cornea. For example, a spherical aberration metric or a pupil metric can be used to design an optimal IOL or an accommodating IOL. A population mean can be determined, and an IOL design can be optimized so as to correct or treat a certain amount of spherical aberration for an optimal or specific pupil size. As shown here, as the diopter of the accommodation task increases, the spherical aberration increases, and the pupil size decreases. By determining a relationship between these factors, it is possible to derive the accommodation zero point from the line based on the mesopic pupil size of the patient, where the mesopic pupil size corresponds to the eye is a normal unaccommodated condition. In some embodiments, it is possible to train down the spherical aberration line, and determine a point where amount of spherical aberration no longer changes when a trial lens power is reduced. This is a point where it is possible to derive the accommodation. In some embodiments, residual accommodation may be used to determine the amount of accommodation desired for an accommodating IOL. It is also possible to design aberration corrections into an accommodating IOL to reduce changing aberrations as the eye accommodates. An amount of spherical aberration can be predesigned for an IOL, such that when the IOL is in an accommodating situation, an amount of spherical aberration is provided for a desired or optimal performance. If the eye exhibits non-linear accommodation, it may be possible to design an accommodating IOL to compensate.

Figure 9:
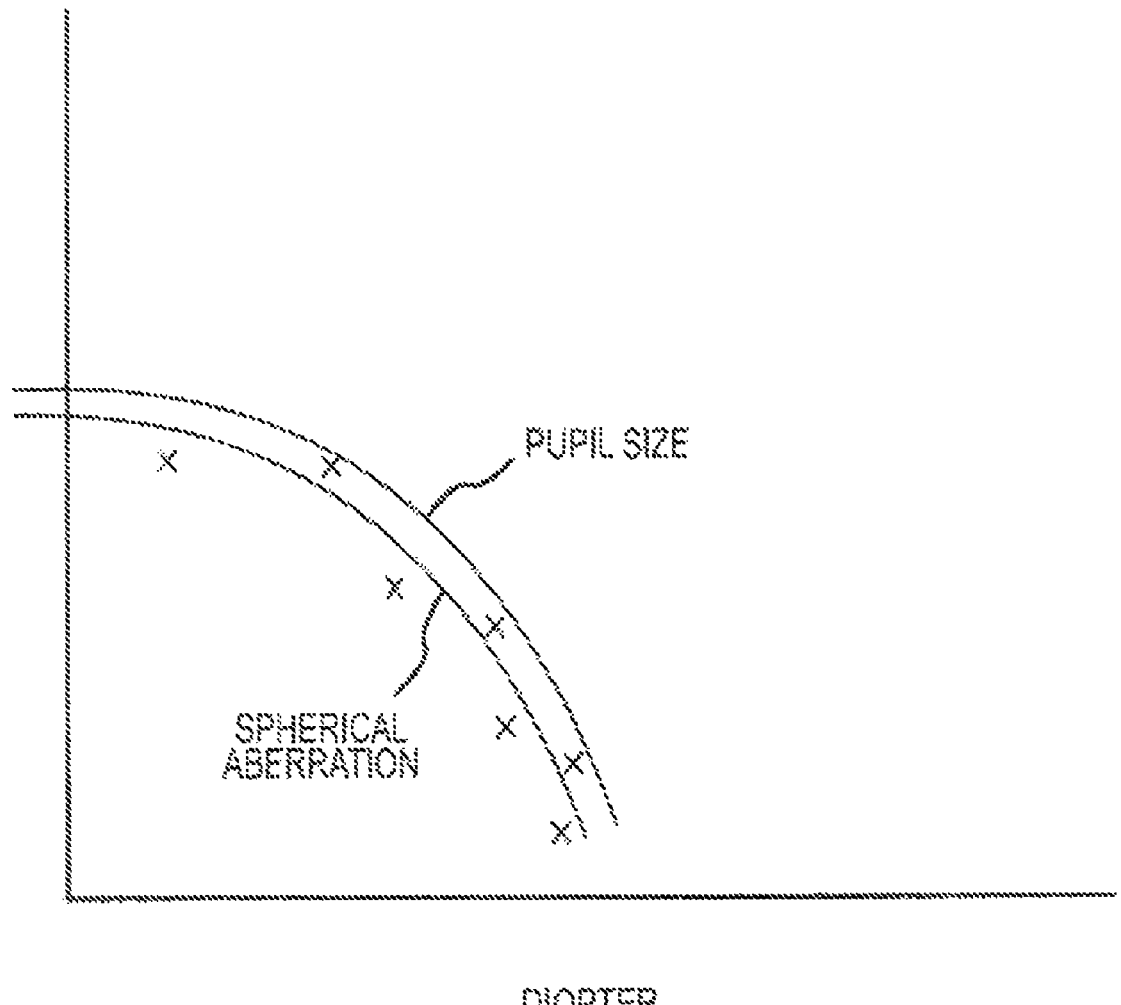
FIG. 9 depicts relationships between accommodation, pupil size, and net spherical aberration according to embodiments of the present invention.

FIG. 9 depicts relationships between accommodation, pupil size, and net spherical aberration according to embodiments of the present invention. A series of accommodations tasks is given to an IOL patient, and a corresponding series of wavefront measurements is taken. The pupil size decreases as the diopter of the accommodation task increases. However, because it may be difficult or impossible for an IOL patient to accommodate, the spherical aberration is observed to decrease as the diopter of the accommodation task increases.

Embodiments of the present invention are well suited for use in designing and developing custom multifocal IOLs, corneal inlays and onlays, and contact lenses. Embodiments of the present invention also encompass systems and methods for developing and designing IOLs and accommodating IOLs. For example, it is possible to evaluate accommodating IOLs after implantation to determine the optimal or desired amount of spherical aberration for an IOL. Data can be re-input or reiterated to refine accommodating IOLs. A population study can be performed for patients who have received implants. Data from the study can be used to determine a spherical aberration that is helpful for a patient. For example, it is possible to determine an amount of spherical aberration for a certain type of accommodating IOL. In many current situations, accommodating IOLs do not include a gradient index material. If an accommodating IOL includes a gradient index material or involves a two piece optic accommodating IOL, there may be a change of spherical aberration. This can mimic a real natural crystalline lens, and can be used for similar studies.

Typically a lens of an eye exhibits a varying gradient index of refraction. In contrast, a polymer-filled bag often has a uniform index of refraction.

Each of the above calculations or operations may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

While the exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A method of determining a vision correction treatment for administration to an eye of a patient, the method comprising:
    obtaining an ocular aberration measurement of a lens of the eye, the ocular aberration measurement based on a first induced metric for the lens that corresponds to a first accommodation state of the eye and a second induced metric for the lens that corresponds to a second accommodation state of the eye; and
    determining a prescription of the vision correction treatment, wherein the prescription is based on the ocular aberration measurement of the lens.

2. The method according to claim 1, wherein the ocular aberration measurement includes a contact lens aberrometer examination.

3. The method according to claim 1, wherein the first induced metric comprises a first induced spherical aberration of the lens and the second induced metric comprises a second induced spherical aberration of the lens.

4. The method according to claim 1, wherein the first induced metric comprises a member selected from the group consisting of a coma metric, a sphere metric, a defocus metric, an astigmatism metric, a trefoil metric, a spherical aberration metric, and a root mean square metric.

5. The method according to claim 1, further comprising providing the treatment to the patient; wherein the treatment includes a contact lens.

6. The method according to claim 1, wherein the treatment comprises a presbyopia treatment.

7. A method of determining an contact lens treatment for an eye of a patient, the method comprising:
    obtaining a natural metric of the eye of the patient, represented at a lens plane of the eye, wherein the natural metric of the eye is based the eye's accommodation response to a diagnostic stimulus; wherein the eye's accommodation response to the diagnostic stimulus is evaluated with a contact lens aberrometer; and
    determining a prescription of a contact lens for the treatment, wherein the contact lens prescription is based on the natural metric of the eye; wherein the natural metric comprises a member selected from the group consisting of a coma metric, a sphere metric, a spherical aberration metric, a defocus metric, a pupil size metric, a low order aberration metric, a high order aberration metric, an astigmatism metric, a trefoil metric, and a root mean square metric.

8. An apparatus for determining an appropriate treatment for an eye of a patient, the eye having a vision deficiency, the apparatus comprising:
    a first input configured to receive a first induced metric for the eye that corresponds to a first viewing condition;
    a second input configured to receive a second induced metric for the eye that corresponds to a second viewing condition;
    a first module configured to determine the difference between the first induced metric and the second induced metric; wherein the first induced metric and second induced metric are represented at a lens plane of the eye of the patient;
    a second module configured to determine an accommodation characteristic of the eye if the difference between the first induced metric and second induced metric does not exceed a predetermined threshold;
    a third module configured to determine a residual accommodation of the eye based on the accommodation characteristic;
    a fourth module configured to receive an ocular aberration measurement of the eye; and
    a fifth module configured to determine a treatment for the eye based on the residual accommodation and the ocular aberration measurement;
    wherein a lens is selected if the residual accommodation of the patient is less than the threshold amount.

9. The apparatus of claim 8, wherein the appropriate treatment includes a presbyopia treatment modality.

10. The apparatus of claim 9 wherein the threshold amount is about 0.5 Diopters.

11. The apparatus of claim 9, wherein the lens is a multifocal contact lens.

12. An apparatus for determining a treatment for administration to the eye of a patient, the apparatus comprising:
    a first input configured to obtain a corneal aberration measurement corresponding to a corneal plane of the eye of the patient;
    a second input configured to obtain a lens aberration measurement of the eye, the ocular aberration measurement based on a first induced metric for the eye that corresponds to a first accommodation state of the eye and a second induced metric for the eye that corresponds to a second accommodation state of the eye;
    a first module configured to determine the aberration of the lens based on a difference between the corneal aberration measurement and the lens aberration measurement, wherein the difference is represented at a peripheral lens plane of the eye of the patient; and
    a second module configured to determine a prescription of a lens for the treatment.

13. The apparatus of claim 12, wherein the lens prescription is a contact lens prescription based on a contact lens aberration measurement.

14. The apparatus of claim 13, wherein the first input is a topography device.

15. The apparatus of claim 13, wherein the first induced metric comprises a first induced spherical aberration of the lens and the second induced metric comprises a second induced spherical aberration of the lens.

16. The apparatus of claim 13, further comprising a third module configured to determine a treatment for the eye of the patient based on the aberration of the lens.

17. The apparatus according to claim 16, further comprising a fourth module configured to provide treatment to the eye of the patient.

18. The apparatus according to claim 17, wherein the provided treatment is a presbyopia treatment.

19. An ophthalmic system for treating presbyopia in an eye of a patient, the system comprising:
    a computer including:

a) processor configured to communicate with at least one peripheral device via a bus subsystem; wherein the peripheral device includes a memory subsystem, a file storage subsystem, a user interface input device, a user interface output device or a network interface subsystem;

b) a network interface subsystem configured to communicate to outside networks;

c) a wavefront measurement system, wherein the wavefront measurement system includes:

a) a first input configured to receive a first induced metric for the eye that corresponds to a first viewing condition;

b) a second input configured to receive a second induced metric for the eye that corresponds to a second viewing condition;

c) a first module configured to determine the difference between the first induced metric and the second induced metric; wherein the first induced metric and the second induced metric are represented at a lens plane of the eye of the patient; and an output coupled to the computer and adapted to provide a lens prescription for the eye of the patient based on the difference between the first induced metric and the second induced metric.

20. The ophthalmic system according to claim 19, wherein the first induced metric for the eye includes lens decentration and the second induced metric for the eye includes spherical aberration; and further wherein the lens prescription is a contact lens prescription.

\* \* \* \* \*